(12) United States Patent
Bevilacqua et al.

(10) Patent No.: US 6,850,656 B1
(45) Date of Patent: Feb. 1, 2005

(54) METHOD AND APPARATUS FOR MEASURING LOCALLY AND SUPERFICIALLY THE SCATTERING AND ABSORPTION PROPERTIES OF TURBID MEDIA

(75) Inventors: Frédéric Bevilacqua, Irvine, CA (US); Christian Depeursinge, Lausanne (CH)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 0 days.

(21) Appl. No.: 09/806,831

(22) PCT Filed: Oct. 7, 1999

(86) PCT No.: PCT/CH99/00476

§ 371 (c)(1),
(2), (4) Date: Apr. 5, 2001

(87) PCT Pub. No.: WO00/20843

PCT Pub. Date: Apr. 13, 2000

Related U.S. Application Data

(60) Provisional application No. 60/103,559, filed on Oct. 7, 1998.

(51) Int. Cl.[7] ............................................. G02B 6/00
(52) U.S. Cl. ..................... 385/12; 356/446; 356/445; 356/432; 356/12
(58) Field of Search ...................... 385/12, 5, 7, 31, 385/35, 40, 54, 56, 116, 147, 39; 356/446, 445, 432; 702/75, 76, 66, 19, 49, 189, 411.5, 411.6, 413.1, 413.4, 417

(56) References Cited

U.S. PATENT DOCUMENTS

| | | | |
|---|---|---|---|
| 5,284,137 A | | 2/1994 | Kessler et al. |
| 5,353,790 A | * | 10/1994 | Jacques et al. ............ 600/315 |
| 5,441,054 A | * | 8/1995 | Tsuchiya .................... 600/310 |
| 5,452,723 A | * | 9/1995 | Wu et al. ................... 600/342 |
| 5,517,987 A | * | 5/1996 | Tsuchiya .................... 600/328 |
| 5,630,423 A | | 5/1997 | Wang et al. |
| 5,645,061 A | | 7/1997 | Kessler et al. |
| 5,676,142 A | | 10/1997 | Miwa et al. |

OTHER PUBLICATIONS

Bevilacqua et al, "In vivo local determination of tissue optical properties", SPIE, European Biomedical Optics, Bios Europe 97, vol. 3194, 1997, pp. 262–268.

Marquet et al, "Determination of Reduced Scattering and Absorption Coefficients by a Single Charge–Coupled–Device Array Measurement. Part I: comparison between experiments and simulations", Optical Engineering, vol. 34, No. 7, Jul. 1995, pp. 2055–2063.

Wyman et al, "Similarity relations for the interaction parameters in radiation transport", Applied Optics, vol., 28, No. 24, Dec. 15, 1989, pp. 5243–5429.

* cited by examiner

*Primary Examiner*—Frank G. Font
*Assistant Examiner*—Kevin C Kianni
(74) *Attorney, Agent, or Firm*—Nixon & Vanderhye, PC

(57) ABSTRACT

We present a method and apparatus for local and superficial measurement of the optical properties of turbid media. The depth probed is on the order of 1 transport mean free path of the photon. The absorption coefficient, reduced scattering coefficient and the phase function parameter $\gamma=(1-g_2)/(1-g_1)$ are optical parameters computed from a single measurement of the spatially resolved reflectance close to the source. Images of superficial structures of the medium can be obtained by performing multi-site measurements. An important application of this technique is the characterization of biological tissues, for example for medical diagnostic purposes. Measurements on biological tissues can be achieved using a probe of diameter less than 2 mm, and the average volume probed is on the order of 1 $mm^3$. Separate images of absorption and tissue structure can be achieved with a resolution of approximately one transport mean free path of the considered tissue.

21 Claims, 15 Drawing Sheets

Fig. 5.b
Apparatus:
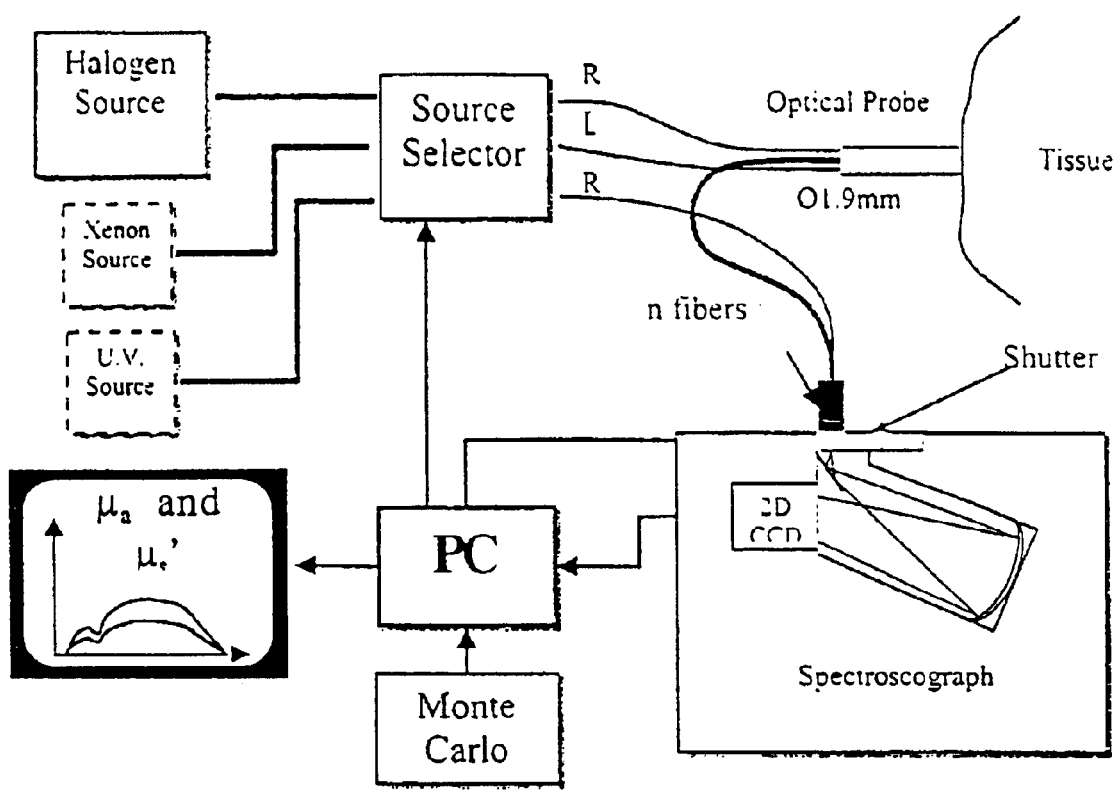
Details of the optical probe:
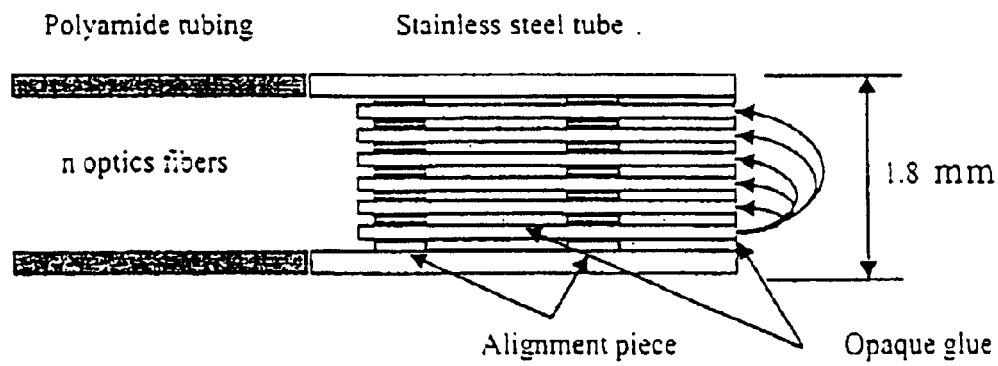

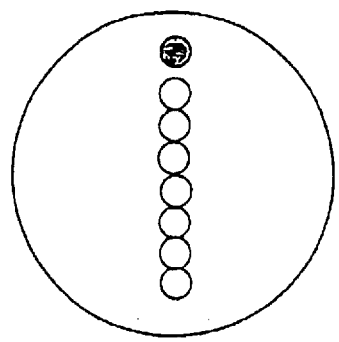

Fig.6a

● detecting fibers
○ illuminating fibers
or
● illuminating fibers
○ detecting fibers

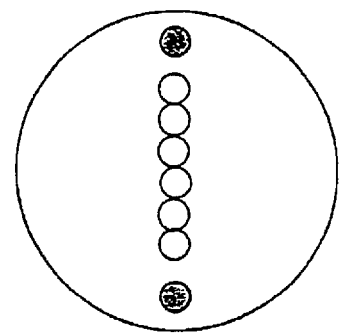

Fig. 6b

● detecting fibers
○ illuminating fibers
or
● illuminating fibers
○ detecting fibers

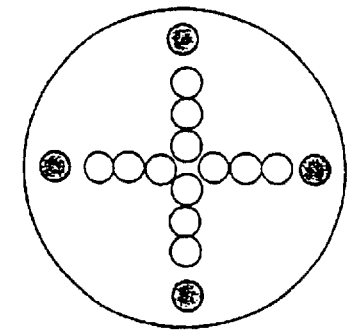

Fig. 6c

● detecting fibers
○ illuminating fibers
or
● illuminating fibers
○ detecting fibers

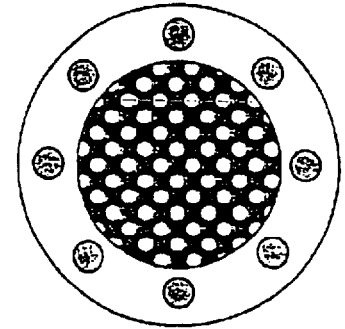

Fig.6d

● single core fiber (detection or illumination)

● multicore fiber or bundle of optical fibers (detection or illumination)

I: Illuminating fibers
C: detecting fibers
F: additional fibers

METHOD AND APPARATUS FOR MEASURING LOCALLY AND SUPERFICIALLY THE SCATTERING AND ABSORPTION PROPERTIES OF TURBID MEDIA

This application is the national stage of PCT/CH99/00476, filed Oct. 7, 1999, which claims the benefit of Provisional Application No. 60/103,559, filed Oct. 7, 1998.

1. FIELD OF THE INVENTION

The present invention relates to a method and an apparatus to quantify the optical scattering and absorption properties of turbid media, that can be applied in the extended optical domain of electromagnetic waves from far infrared (up to the microwave domain) to the far UV domain, i.e. where the energies of the photons composing the electromagnetic waves range from a few milli-electron-Volt to more than ten electron-Volt. More precisely the present invention relates to a non-invasive measurement, over a small area of the sample surface. Local and superficial characterization of biological tissues in vivo is a major application of this invention.

2. RELATED BACKGROUND ART

Different techniques have already been proposed to quantitatively determine the absorption and reduced scattering coefficients of turbid media. See Welch, A. J.; van Gemert, M. J. C., Optical Thermal Response of Laser Irradiated Tissue; Plenum Publishing Corp., New York, 1995, and references therein. Most of the non-invasive methods are based on the measurement of spatially and/or temporally-resolved reflectance. The principle is as follows: the turbid medium is illuminated by a collimated or focused light source. The backscattered light is measured by one or several detectors. Different types of measurements are possible, depending on the time-dependence of the illuminating source: steady-state (continuous source), time-domain (short pulsed source) or frequency domain (amplitude modulated source). The present invention relates to the case of steady-state measurements, performed at different distances $\rho$ between the source and the detectors. However, the technique presented here can be complemented by time- or frequency-domain measurements.

The range of $\rho$ values is an important point to consider, when comparing different methods based on the measurement of the reflectance. First, the probed volume of the turbid medium is related to the source-detector separation $\rho$. The larger the source-detector separation, the deeper the average depth probed. Second, depending on the range of $\rho$, different mathematical processing must be used to obtain the optical properties from the raw data.

At least two cases must be distinguished.

1) The first case corresponds to source-detector separations larger than several transport mean free paths. For typical biological tissue optical properties (W. -F. Cheong, S. A. Prahl, and A. J. Welch, "A Review of the Optical Properties of Biological Tissues," IEEE J. Quantum Electron. 26, 2166–2185 (1990)), this case corresponds to a source-detector separation larger than 2 mm. An analytical form of the reflectance can be obtained from the diffusion equation, if the absorption coefficient $\mu_a$ is sufficiently lower than the scattering coefficient $\mu_s$ (typically ten times). In such a case, the relevant optical properties are the refractive index, the absorption coefficient and the reduced scattering coefficient. The average depth of probing is on the same order as the source-detector separation $\rho$.

Such methods have been already published, and are the object of patents (Ref., U.S. Pat. No. 5,517,987 Tsuchiya, U.S. Pat. No. 5,676,142 Miwa et al.).

2) The second case corresponds to source-detector separations close to one transport mean free path. For biological tissues[2], such source-detector separations correspond typically to distances from 0.1 to 2 mm. The average depth probed is on the order of 1 mm. Such small source-detector separations enable the measurement of the optical properties of a small tissue volume.

Wang et al. (U.S. Pat. No. 5,630,423) proposed a method for the determination of the reduced scattering coefficient only, using an optical beam of oblique incidence. Moreover, their analysis does not include the effect of the phase function. Kessler et al. (U.S. Pat. Nos. 5,284,137 and 5,645,061) proposed a method for measuring the local dye concentration and scattering parameters in animal and human tissues, based on spatial and spectral measurements. However, their methods do not enable the simultaneous determination of the absorption coefficient, reduced scattering coefficient. Other publications may be of concern:

1. See "Welch, A. J.; van Gemert, M. J. C. Optical Thermal Response of Laser Irradiated Tissue; Plenum publishing Corp., New York, 1995", and references therein.
2. W. -F. Cheong, S. A. Prahl, and A. J. Welch, "A Review of the Optical Properties of Biological Tissues," IEEE J. Quantum Electron. 26, 2166–2185 (1990).

3. SUMMARY OF THE INVENTION

In the case of source-detector separations close to one transport mean free path, light propagation has been modeled using Monte Carlo simulations. In contrast to the previous case where the source-detector separation is larger than several transport mean free paths, it was discovered by the inventors that not only the first moment of the phase function must be considered, but also the second moment. More precisely, the relevant optical properties are the refractive index, the absorption, the reduced scattering coefficient and a new parameter $\gamma=(1-g_2)/(1-g_1)$, that takes into account the first two moments of the phase function, denoted $g_1$ and $g_2$ respectively.

Different methods have been proposed for local characterization of turbid media, and in particular of biological tissues. Nevertheless none allows for the simultaneous determination of the absorption, the reduced scattering coefficient and the parameter $\gamma$.

In the present invention we present a method and apparatus for the measurement of the absorption coefficient, the reduced scattering coefficient and the said phase function parameter $\gamma$, from the spatially-resolved reflectance data at short source detector separation. These three parameters, which can be measured at different wavelengths, enable us to characterize turbid media, such as biological tissues. Our method is based on a theoretical study of the reflectance at short source-detector separations, that we performed with Monte Carlo simulations.

BRIEF DESCRIPTION OF THE DRAWINGS

FIG. 5.b. Basic description of the apparatus: Particular embodiment where the probe is composed of n detecting fibers (typically 6) in parallel. A broadband or white light source is used for excitation and the retro-diffused light is collected by the n detecting fibers in parallel and dispersed in parallel in a spectrograph, before being detected on a 2D CCD camera and transmitted numerically to a PC for $\gamma, \mu'_s, \mu_a$ determination at each wavelength $\lambda$.

FIG. 5.c. Basic description of the apparatus. Case of a measurement with sources and detectors directly in contact with the turbid medium.

FIG. 5.d. Basic description of the apparatus. Case of non-contact measurements with a 1D or 2D detector, coupled with an imaging device. Scanning systems 1 and 2 are optional, they may be distinct from one another or confounded in a single scanner.

FIG. 5.e. Basic description of the apparatus. Case of non-contact measurements with source and detection beams deflected by one or two scanning devices which may be distinct from one another or confounded.

6a. Simple arrangement for a single measurement.

6b. Arrangement for symmetrical measurements.

6c. Arrangement for multiple measurements.

6d. Arrangement for multiple measurements, using an multicore fiber, or an optical fiber bundle.

6e. Arrangement for symmetrical measurements where detecting fibers are arranged on an elliptic path so as giving a regular spacing from the illuminating fibers to the detecting fibers, while maximizing the collecting surface of the fibers. Additional fibers F can be put in the center of the probe or around the probe for other light channels: collecting fibers for fluorescence or Raman scattering for example.

Figure 6E:
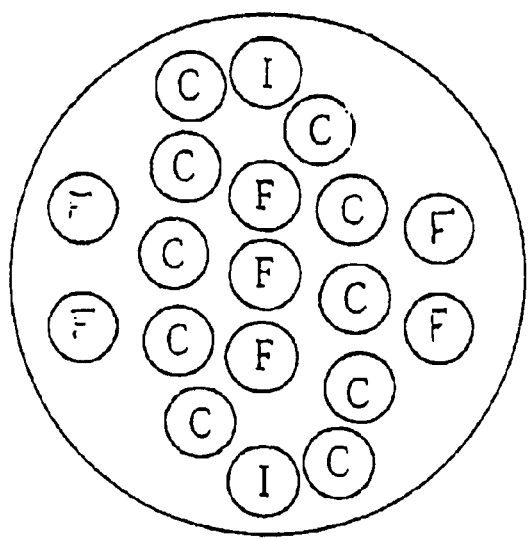
FIG. 6. Examples of the sample side of the fiber optical probe.
Figure 7:
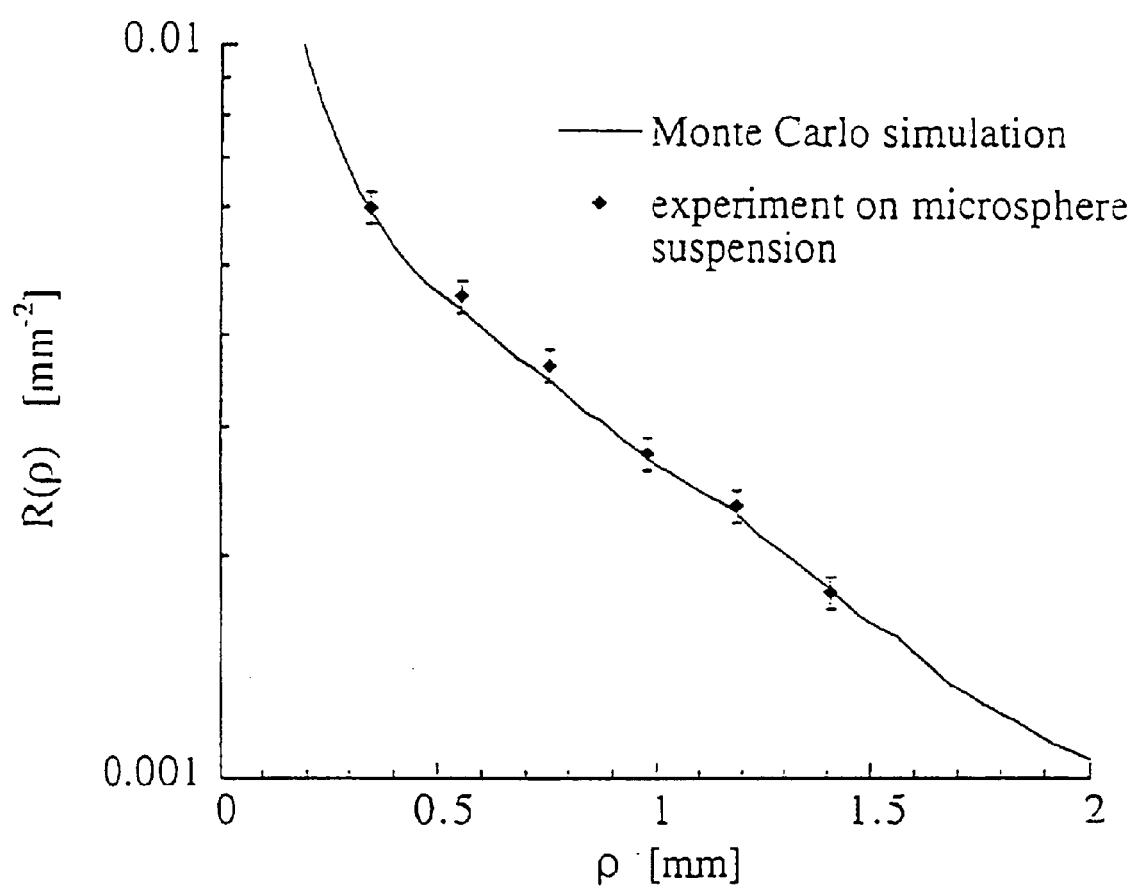

FIG. 7. Example of a measurement of the spatially-resolved reflectance with the probe shown in FIG. 6.a. The measurement, performed on a microsphere suspension, is superimposed to a Monte Carlo simulation. The optical properties, computed from published water optical properties ($\mu_a$) and Mie theory ($\mu'_s, \gamma$) are: n=1.33, $\mu_a$=0.0004 mm$^{-1}$, $\mu'_s$=1.0 mm$^{-1}$, $\gamma$=2.2. The calibration was performed with a siloxane sample of known optical properties.

Figure 8:
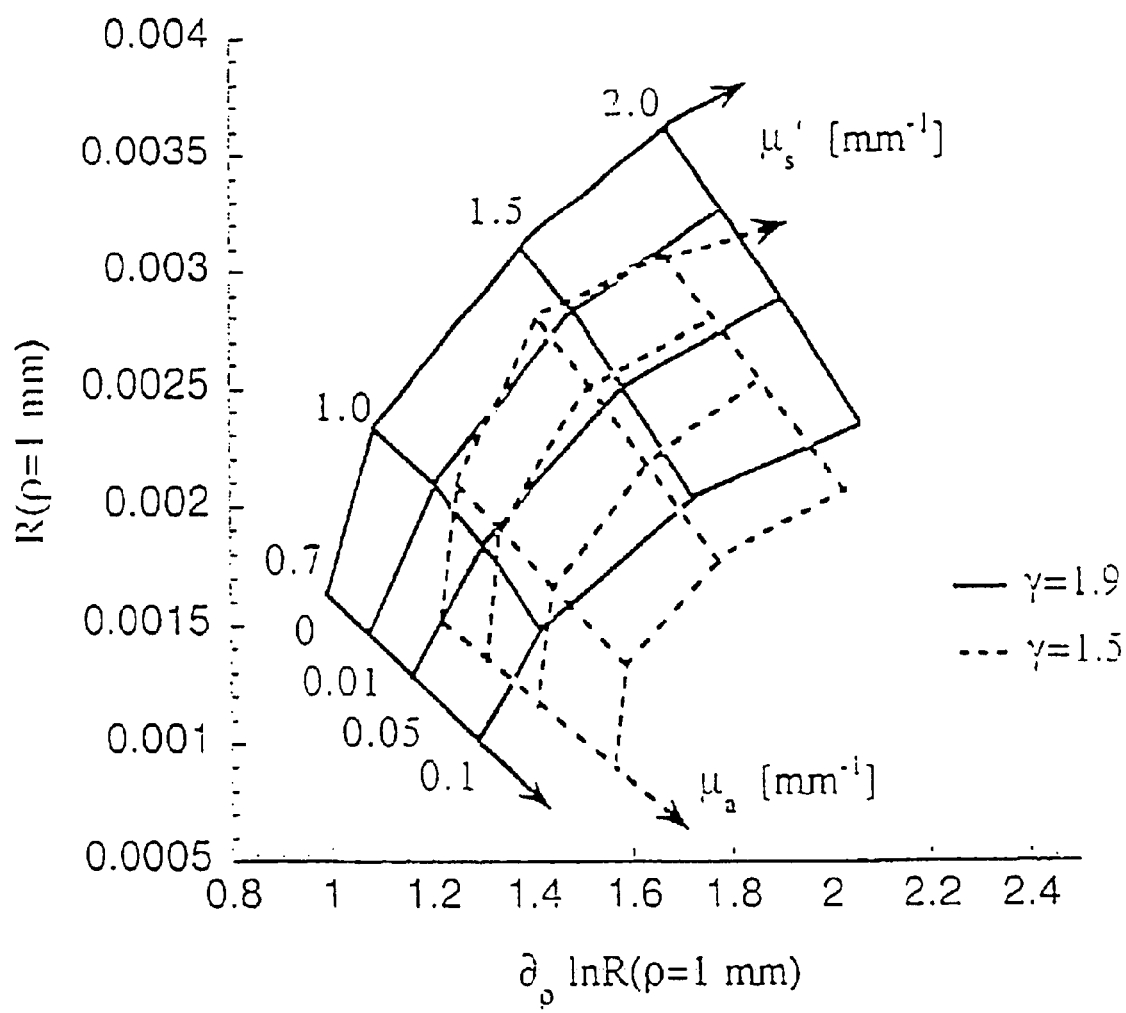

FIG. 8. Relation between the parameters $R(\rho=1 \text{ mm})$ and $|\partial\rho\ln R(\rho=1 \text{ mm})|$ and the optical coefficients $\mu'_s$ and $\mu_a$. Case of $\gamma=1.5$ and 1.9. Probe of refractive index=1.5, sample of refractive index=1.4, optical fibers diameter=200 $\mu$m, NA=0.37 (source and collection).

Figure 9:
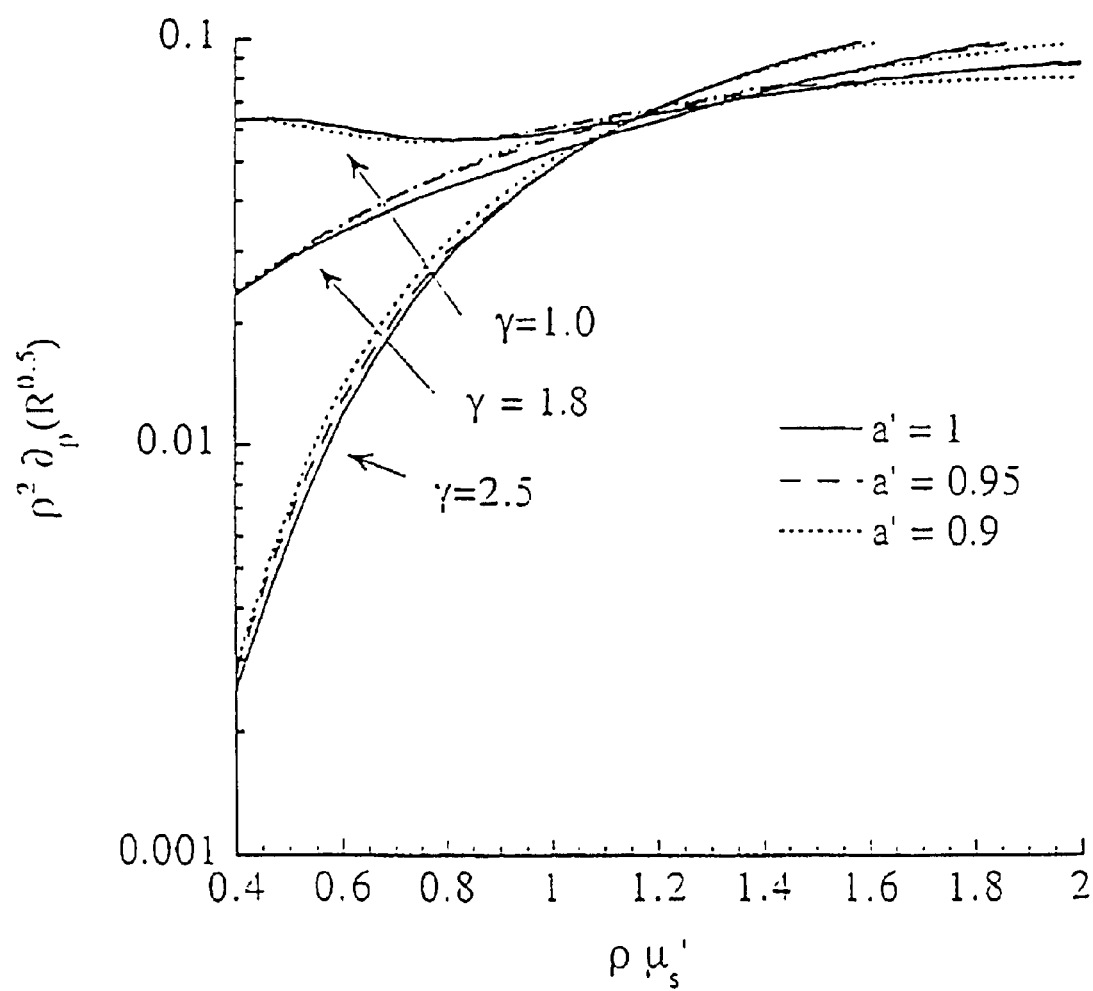

FIG. 9. Plot of the parameter $$\frac{\partial}{\partial \rho}\sqrt{R}$$

for different $\gamma$ values (1.0, 1.8, 2.5), different reduced albedo a' (1, 0.95, 0.9) and for fixed $\rho=1$ mm. Mismatched refractive index n=1.4.

Figure 10:
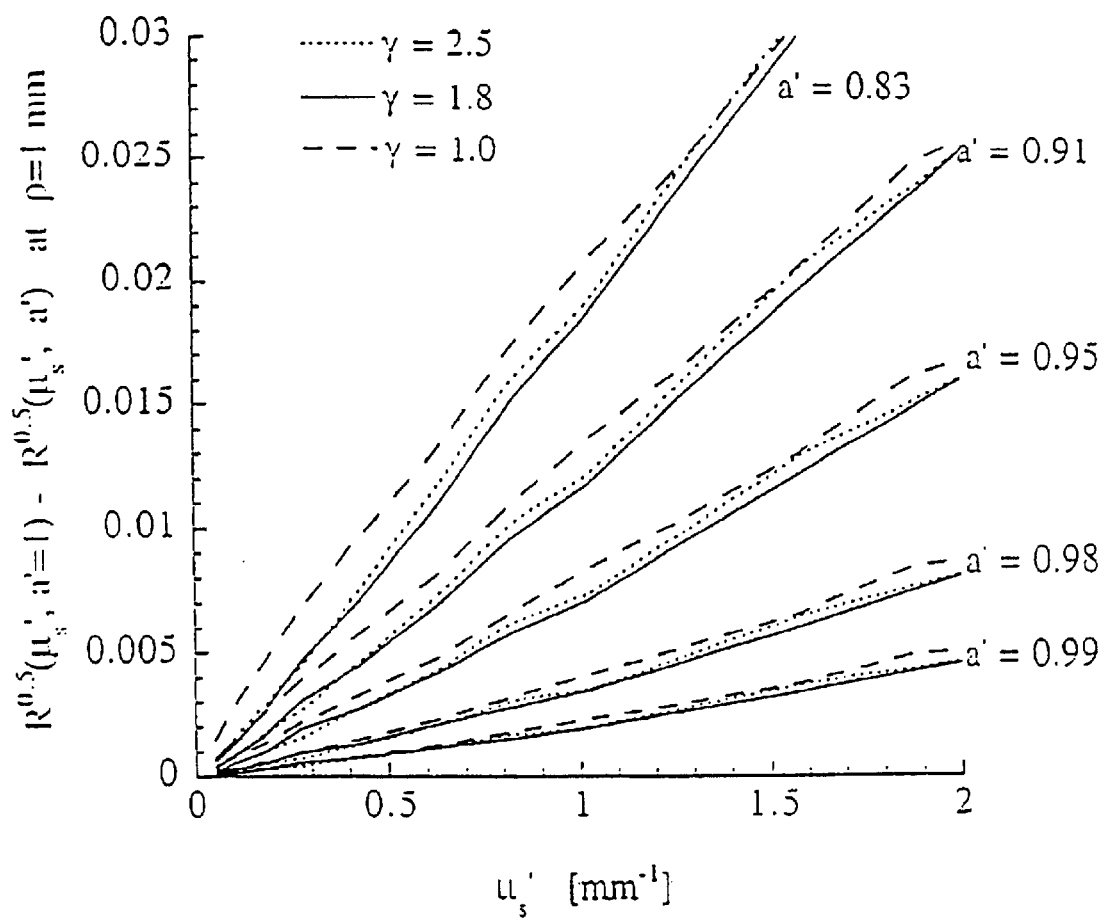

FIG. 10. Plot of $\sqrt{R(a'=1)}-\sqrt{R(a')}$ for different $\gamma$ values and reduced albedo a', and for fixed $\rho=1$ mm. Mismatched refractive index n=1.4.

DETAILED DESCRIPTION OF THE INVENTION

1. Definitions

The present definitions are given for clarity of the concepts developed in the parent and are worded in agreement with Welch, A. J.; van Gemert, M. J. C., Optical Thermal Response of Laser Irradiated Tissue; Plenum Publishing Corp., New York, 1995, and references therein.

Figure 1:
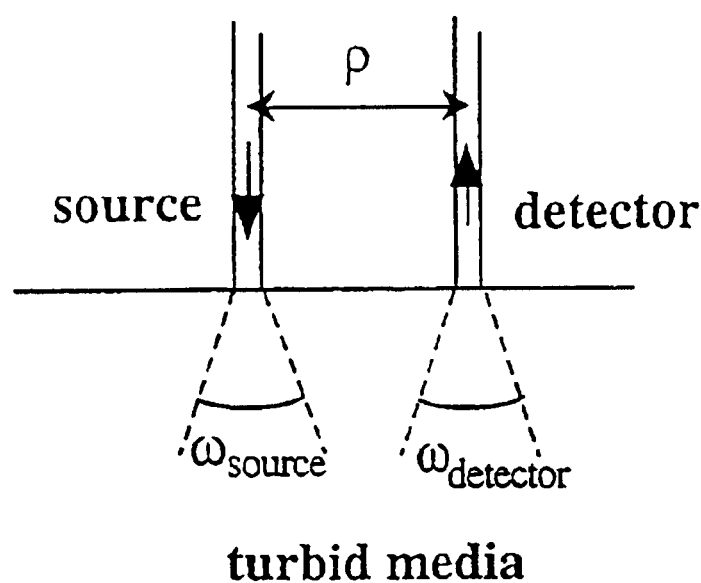
FIG. 1. Description of the principle of spatially-resolved reflectance measurement. $\rho$ denotes the source–detector distance, $\omega_{source}$ and $\omega_{detector}$ are the solid angles of light acceptance determined by the Numerical Apertures (N.A.) of the optical fibers.
Figure 1:
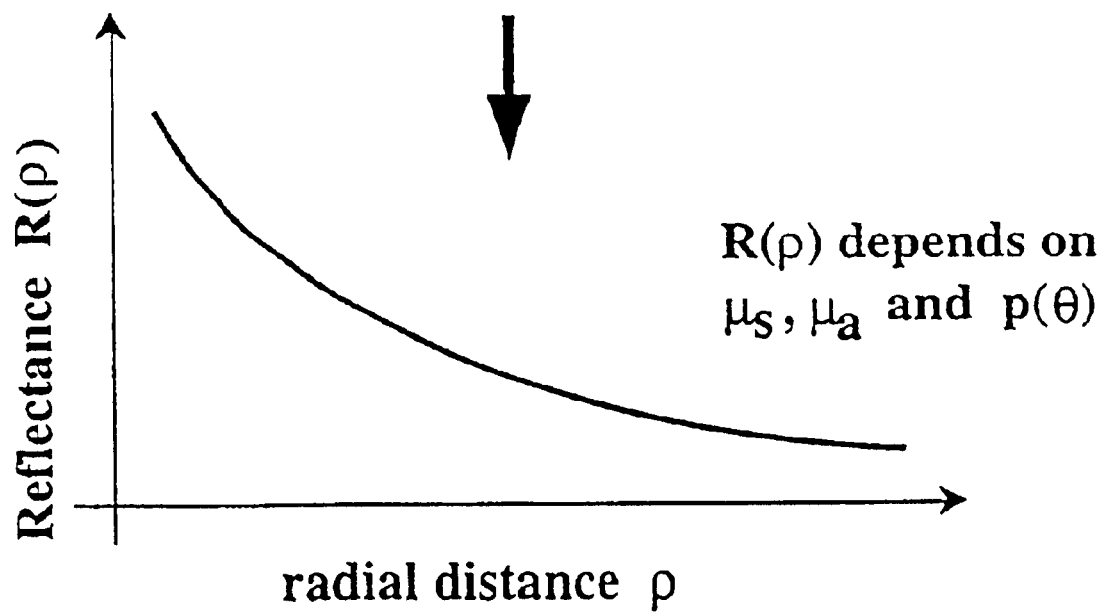

The concept of spatially resolved reflectance is illustrated in FIG. 1. Consider a collimated light beam impinging on a turbid medium (through air or through a light guide, or even generated locally), in a given solid angle $\omega_{source}$ determined by the Numerical Aperture of the illuminating fiber: N.A. which is defined as the half angle of the entrance angle in the fiber, and on a limited area $A_{source}$, where the source irradiate the surface. The spatially resolved reflectance $R(\rho)$ is defined by the backscattered light power in a given solid angle $\omega_{detector}$, at a distance $\rho$ from the source, per unit area and normalized by the source power. The collecting area of the detector or detecting fiber is $A_{detector}$. The distance $\rho$ is referred as the source-detector separation (also in the case when light guides or imaging devices are used for the illumination and for the collection of the backscattered light).

$R(\rho)$ depends on the optical properties of the turbid medium, defined below. Note that $R(\rho)$ depends also on the source and detectors characteristics, i.e. numerical aperture and sizes. In a general situation, $R(\rho)$ is the result of the convolution of the corrected reflectance curve and the source irradiance and detector sensitivity over, respectively, the surfaces $A_{source}$ and $A_{detector}$. When $A_{source}$ and $A_{detector}$ are smaller than the required spatial resolution, $R(\rho)$ is confounded with the corrected spatially resolved reflectance.

It is commonly admitted that the fundamental optical properties of a turbid medium is determined by the average index of refraction n of the medium, the absorption coefficient $\mu_a$, the scattering coefficient $\mu_s$, and the phase function $p(\theta)$ where $\theta$ is the scattering angle. The absorption coefficient $\mu_a$ [mm$^{-1}$] is defined as the probability of absorption per unit infinitesimal pathlength. The scattering coefficient $\mu_s$ [mm$^{-1}$] is the scattering probability per unit infinitesimal pathlength. The phase function $p(\theta)$ is the density probability function for the scattering angle $\theta$. The phase function is normalized as follows:

$$1 = 2\pi \int_0^\pi p(\theta) \sin\theta d\theta \quad (1.1)$$

In turbid media and in biological tissues in particular, the phase function $p(\theta)$ is a continuous function of the scattering angle $\theta$ and generally depends on the dielectric properties and on the material microstructure. It can be approximated by a development in Legendre polynomials:

$$p(\theta) = \frac{1}{4\pi} \sum_{n=0}^{\infty} (2n+1)g_n P_n(\cos\theta) \qquad (1.2)$$

Where $g_n$ is the $n^{th}$ order moment of the phase function and $P_n(\theta)$ is the Legendre polynomial of order n:

$$g_n = 2\pi \int_0^\pi P_n(\theta)p(\theta)\sin\theta d\theta \qquad (1.3)$$

The first moment of the phase function is also called the anisotropy factor, and is often simply noted g ($=g_1$). It represents the mean cosine of the scattering angle. The reduced scattering coefficient $\mu_s'$ is defined as:

$$\mu_s' = \mu_s(1-g_1) \qquad (1.4)$$

The transport mean free path (or reduced mean free path) mfp' of the photons, in a turbid medium, is defined as:

$$mfp' = (\mu_s' + \mu_a)^{-1} \qquad (1.5)$$

The reduced albedo a' is the ratio:

$$a' = \mu_s'/(\mu_s' + \mu_a) \qquad (1.6)$$

As a result of the present invention described in more details in the next section, it is also necessary to define another phase function parameter called $\gamma$.

$$\gamma = (1-g_2)/(1-g_1) \qquad (1.7)$$

All the parameters listed above are referred as optical properties. They are wavelength dependent, and can vary in space and time. In the following, $\gamma$, $g_1$ and $g_2$ will be considered as parameters characterizing the turbid medium.

2. Reflectance Measurements at Distances Close to One Transport Mean Free Path

The methods described in U.S. Pat. No. 5,517,987 (Tsuchiya) are based on measurements with a large range of source-detector separations, typically from 1 mfp' to 10 mfp'. In such cases, the volume probed is on the order of 10–1000 (mfp'). In contrast with such a large scale investigation, the present invention is directed to a novel approach where the volume probed is much smaller, on the order of 1 (mfp'). This is achieved by using only small source detector separations, typically from 0.1 to 2 mfp'. The lateral dimension of probing is limited to this range of distances.

Note that the present invention can be complemented by large source-detector separation measurements, if the optical properties of both superficial and deep parts of a turbid medium must be determined.

A model of photon migration in tissue was necessary to predict the relationship between the measured reflectance and the optical properties. Analytical solutions from the diffusion equation are not appropriate in our case because we are interested in the reflectance close to the source, at distances comparable to the transport mean free path [mfp']. We have performed Monte Carlo simulations to predict the measured reflectance of an homogeneous semi-infinite turbid media.

The exact diameter of the illuminating and collecting fibers, as well as their Numerical Apertures (N.A.), have been taken into account in the simulations. The mismatch of index of refraction at the surface of the medium have been also taken into account in the simulations, by using the Fresnel law for each photon reaching the surface.

Figure 2:
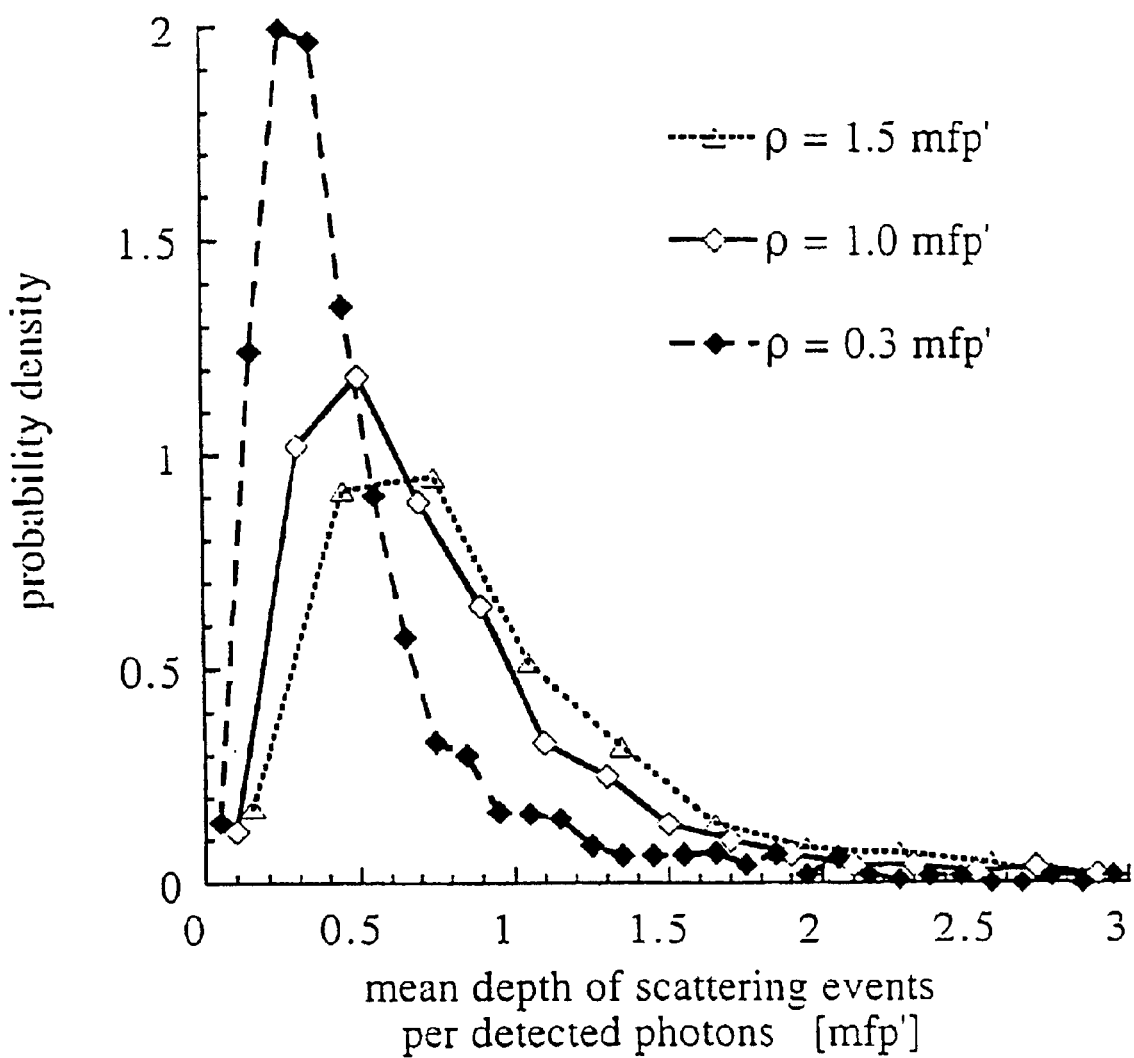
FIG. 2. Probability density function of the mean depth of scattering events per detected photons.

This is also one result of this simulation to compute the average depth of probing, illustrated in FIG. 2. It is demonstrated that only the superficial part of the turbid medium is probed if small source-detector separations are used. For this, we determined the depth below the surface of each scattering event in the simulation. With this information we determined the average depth of all the scattering events for each detected photon, which we present as a probability density function in FIG. 2. This figure shows that the average depth of scattering is approximately around 1 mfp'. Moreover it showed that the part located below 2 mfp' was not playing a significant role in the measured signal (for $\rho$<1.5 mfp').

The spatially resolved reflectance R($\rho$), with short source-detector separations is more complex than in the case of large source-detector separations. Indeed, for small source detector-separation conditions, the inverse problem, i.e. calculating the localized absorption and reduced scattering coefficients, is sensitive to the scattering phase function. It is part of the present invention to have shown, from Monte Carlo simulations, that only the first and second moments of the phase function can be taken into account. Moreover, it was established that the influence of these two moments are not independent. Indeed, it is a merit of this invention to demonstrate that only one parameter $\gamma=(1-g_2)/(1-g_1)$, which depends on the first and second moments of the phase function can be used to characterize accurately the reflectance at short source-detector separation.

Figure 3:
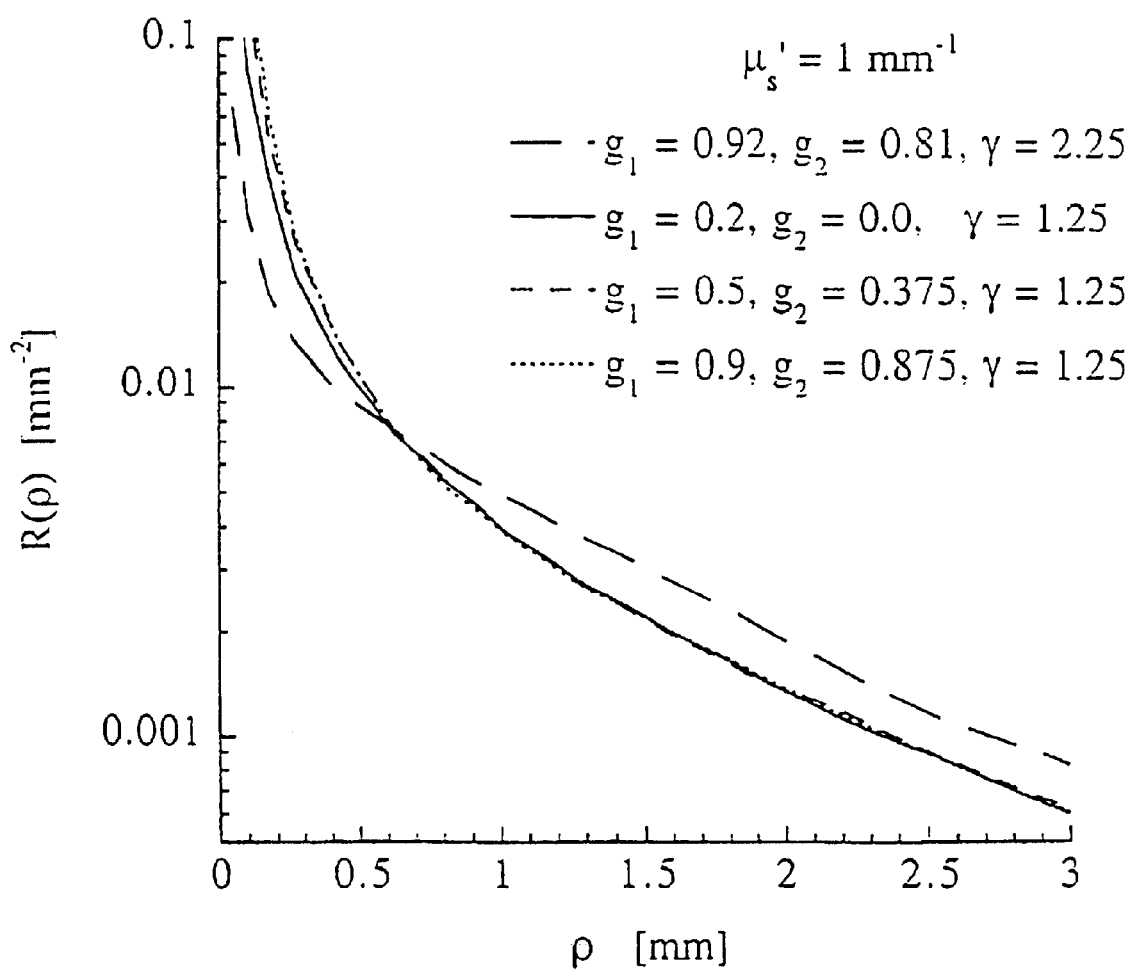
FIG. 3. Examples of spatially resolved reflectance curves obtained with different phase functions. Case of matched refractive index (n=1.0).

FIG. 3 illustrates the fact that the parameter $\gamma$ is the only predominant parameter of the phase function that must be taken into account (and not $g=g_1$ as frequently mentioned in literature). Different reflectance curves, obtained from Monte Carlo simulations are shown in FIG. 3. Four different phase functions were used for the simulations. Three phase functions are characterized by $\gamma=1.25$, but different $g_1$ and $g_2$ values. FIG. 3 shows that almost identical reflectance curves are obtained for distances $\rho\mu_s'>0.3$, if the $g_1$ and $g_2$ are varied in such a way that the parameter $\gamma$ stays constant ($\gamma=1.25$). For comparison, the reflectance computed with a different g ($=g_1$) value is also presented ($\gamma=2.25$). It appears then clearly that the parameter g ($=g_1$) plays a significant role in the reflectance.

The parameter $\gamma$ depends on the characteristics of the set of scatterers inside the turbid medium: shape, distribution of sizes and refractive index.

The possibility of determining this parameter $\gamma$ is an important part of this invention, and has never been reported earlier. The determination of $\gamma$ can be related to the microscopic structure of the sample, since $\gamma$ is related to the sizes and refractive indexes of the scatterers.

In most cases, the average refractive indices n and the source and detectors characteristics are fixed and known. In such case, only three parameters are determined from measurements at short source-detector separation: $\mu_a$, $\mu_s'$ and $\gamma$.

It is important to note that the parameter $\gamma$, cannot be estimated if large source detector separations are used. Indeed, the reflectance is only sensitive to $\gamma$ at short source-detector separation.

It was also derived from Monte Carlo simulations that the reflectance R($\rho$), for $\rho\approx 1$ mfp', can be reasonably well approximated by the expression:

$$R(\rho) \approx [A(\rho, \mu_s', \gamma) + B(\mu_a, \mu_s')]^2 \qquad (1.8)$$

Figure 4:
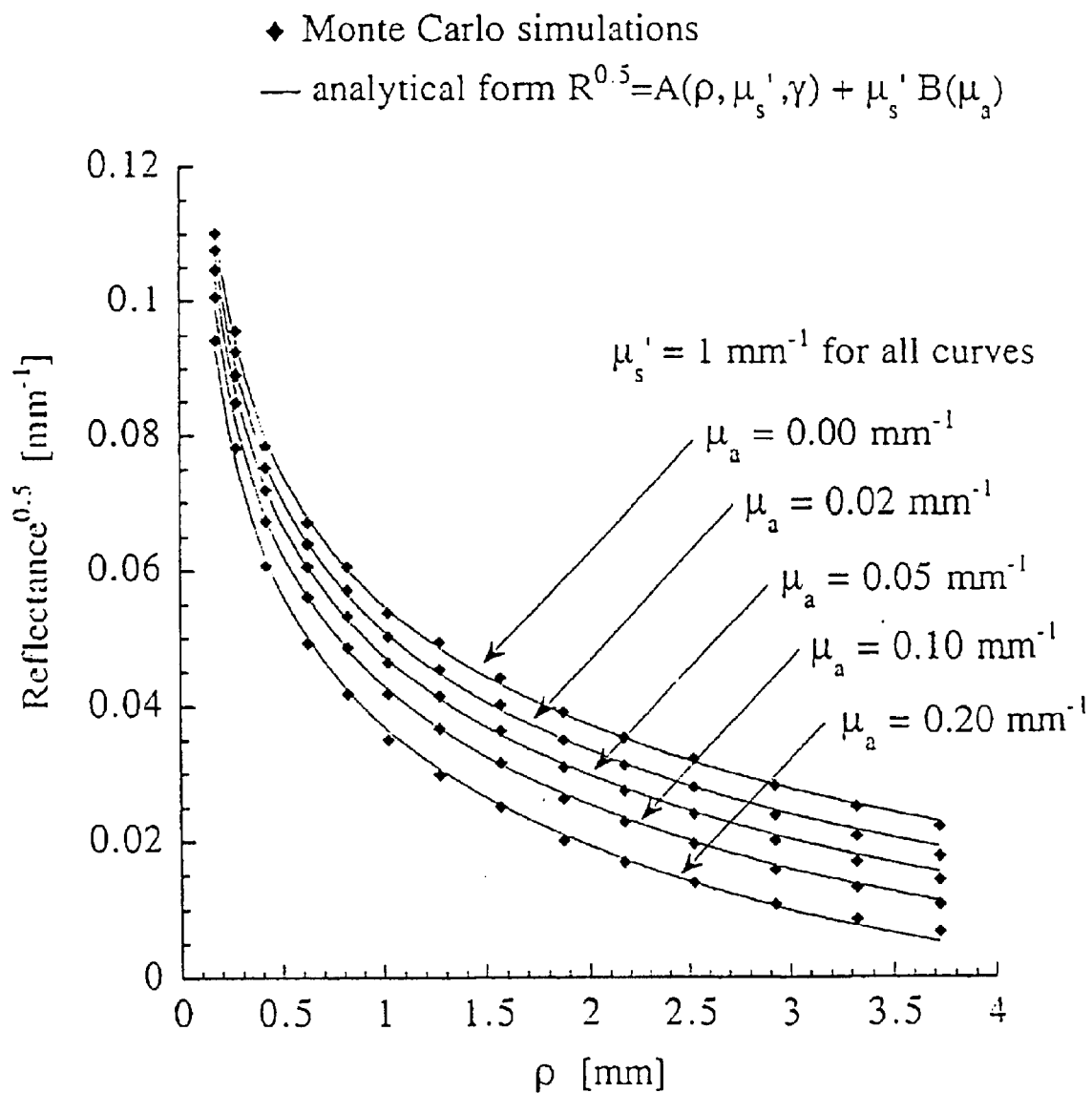
FIG. 4. Monte Carlo simulations and fits of the spatially resolved reflectance curves by mathematical expression in the form $R(\rho) \cong [A(\rho, \mu'_s, \gamma) + \mu'_s B(\mu_a)]^2$. Case of constant $\gamma=1.9$ and $\mu'_s=1$ mm$^{-1}$, numerical aperture of the source and detectors=0.37, $A=0.0647\rho^{0.324}\exp(-0.161\rho)$, $B=0.18653 \mu_a-0.8466 \mu_a^2+1.836 \mu_a^3$.

In many cases, we found that Equ. (1.8) can also be written as:

$$R(\rho) \approx [A(\rho, \mu_s', \gamma) + \mu_s' B(\mu_a)]^2 \qquad (1.9)$$

it is important for the description of the invention to evidence the fact that the function A depends on ρ, the scattering properties (i.e. $\mu_s'$ and γ) but not on $\mu_a$. In contrast, the function B depends on $\mu_a$ and $\mu_s'$ but neither on γ nor ρ. An example of Equ. (1.9) is shown in FIG. 4.

This formulation is of great help to solve the inverse problem, as described in section 5.3.

3. Apparatus

Figure 5A:
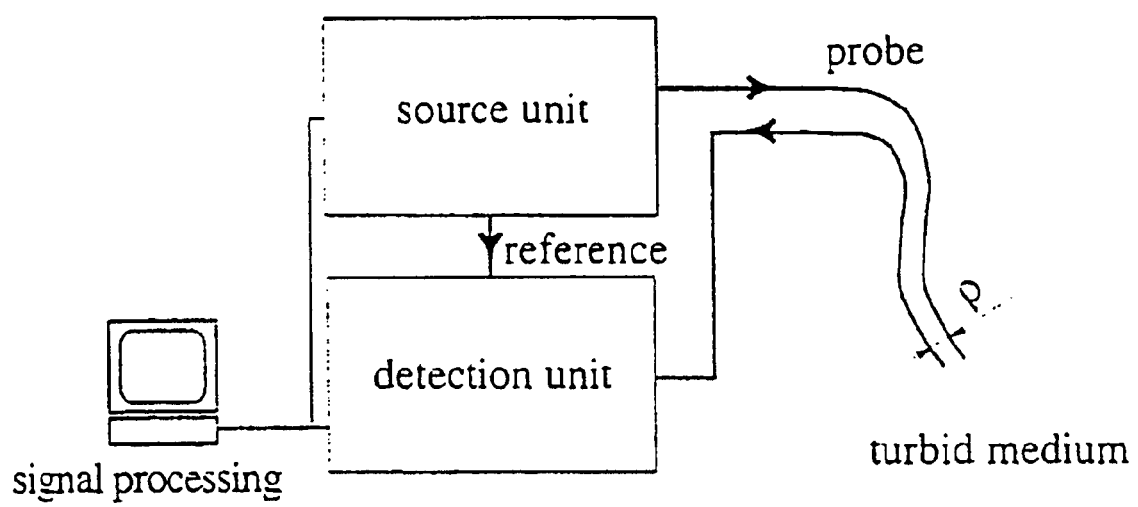
FIG. 5.a. Basic description of the apparatus: Case of measurements with an optical fiber probe. The apparatus comprises a probe connected to a light source unit and a detection unit, both units being connected to a computer or signal processing unit. The optical fiber probe is constituted of one or more illuminating fibers, and one or more collecting fibers.

In the first embodiment, the apparatus can be divided in three parts, described in FIG. 5a.

The first part is the illuminating system. Any light source can be used. For example: a) white sources, such as halogen or xenon lights, metal halides or fluorescent or phosphorescent sources; b) sources such as lasers, laser diodes, optical fiber lasers, light emitting diodes or superluminescent diodes; c) the sources described in points a) and b) where monochromators, filters or interference filters are added to select a given set of wavelengths.

In the first preferred embodiment, the light power is conducted to the investigated sample by the probe, which is the second part of the apparatus. The probe is preferably made of optical fibers, to illuminate and to collect the backscattered light. But GRIN rods or other types of light pipes can also be used. Different possible arrangements of optical fibers are illustrated in FIG. 6. Two different modes of measurements can be chosen. First, one fiber is used to illuminate the sample and at least two other fibers are used to collect the backscattered light at two different distances. Second, one fiber is used to collect the light and at least two other fibers, located at two different distances from the first one, are used to illuminate sequentially the sample.

The arrangement of the different fibers can be replaced by any imaging system or image guide, such as multicore optical fibers, or optical fiber bundle.

The light collected by the probe is analyzed by the detection unit, which is the third part of the apparatus. If wide spectral light sources are used (such as halogen or xenon lights), a spectrograph can be put between the probe and the detector to get wavelength dependence of the backscattered signal (either in the source or detection unit). Any type of detector can be used. For example, photodiodes, avalanche photodiodes or photomultipliers can be assigned to each collecting fiber. Simultaneous detection of each collecting fiber can also be achieved using linear or two-dimensional detectors such as Charge-Coupled Detectors (1D or 2D), intensified CCD or array of photodiodes.

A particular embodiment is described in FIG. 5.b.: the probe is composed of n detecting fibers (typically 6). A broadband or white light source is used for excitation and the retro-diffused light is collected by the n detecting fibers and dispersed in parallel in a spectrograph, before being detected by a 2D CCD camera and transmitted numerically to a PC for γ, $\mu_s'$, $\mu_a$ determination at each wavelength λ. This particular embodiment has the advantage of yielding the wavelength dependence of γ, $\mu_s'$, $\mu_a$ from a single measurement.

Figure 5C:
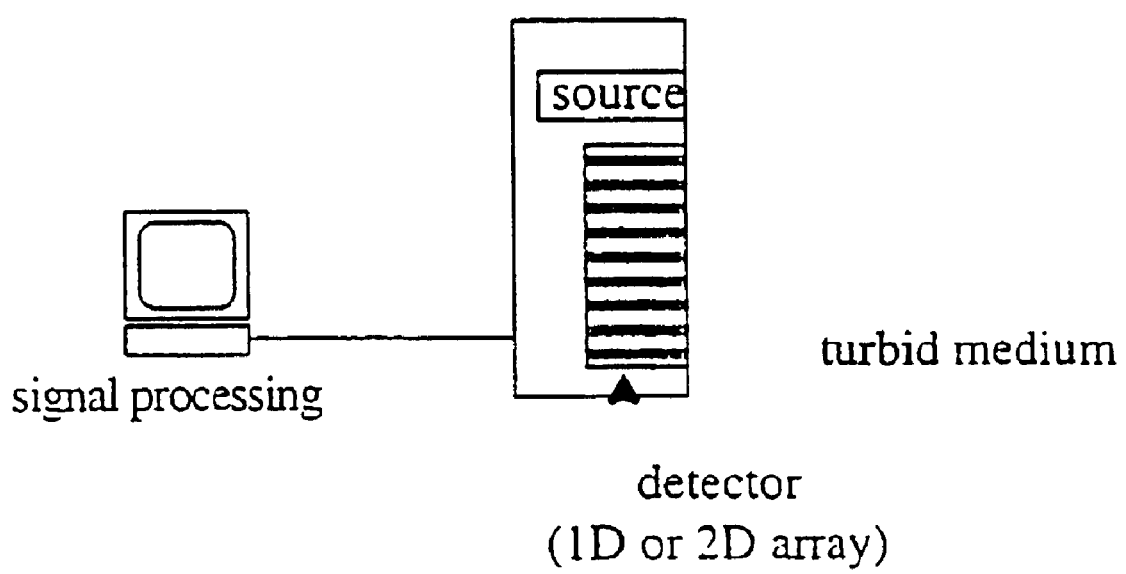

A second type of embodiment is presented in FIG. 5c. The difference with embodiments presented in FIG. 5a and FIG. 5b is that optionally no optical fibers, light pipes or grin rods are used. The light source unit is directly in contact with the turbid medium, as well as the detector unit. Collimating optics, micro-optics or imaging optics (DOE Diffractive Optical Elements for example) can be put between the turbid medium and the actual light sources and detectors. The different type of sources and detectors cited in example for the first embodiment can be used for the second type of embodiments. Hybrid design, such as arrangements involving both direct contact sensors or detectors and fibers, light pipes or grin rods are also included in the present embodiment.

Figure 5D:
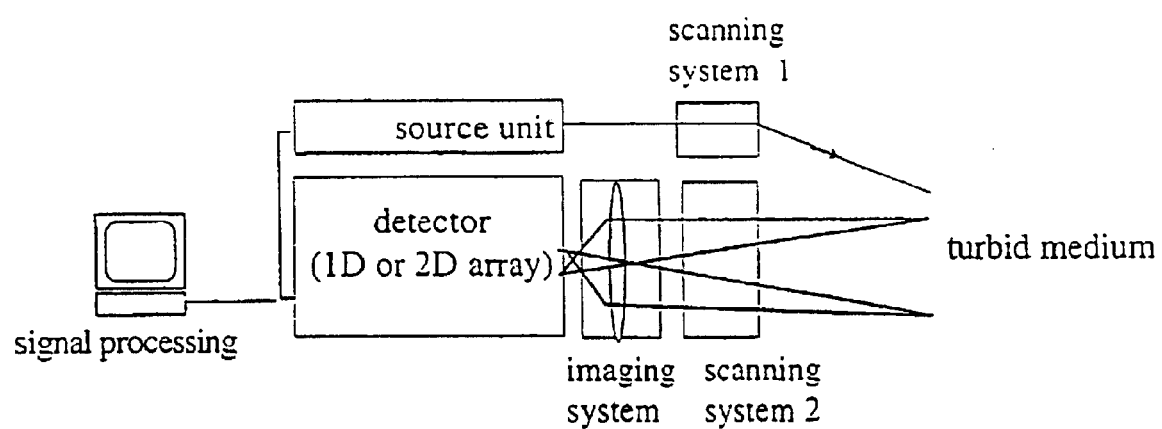
Figure 5E:
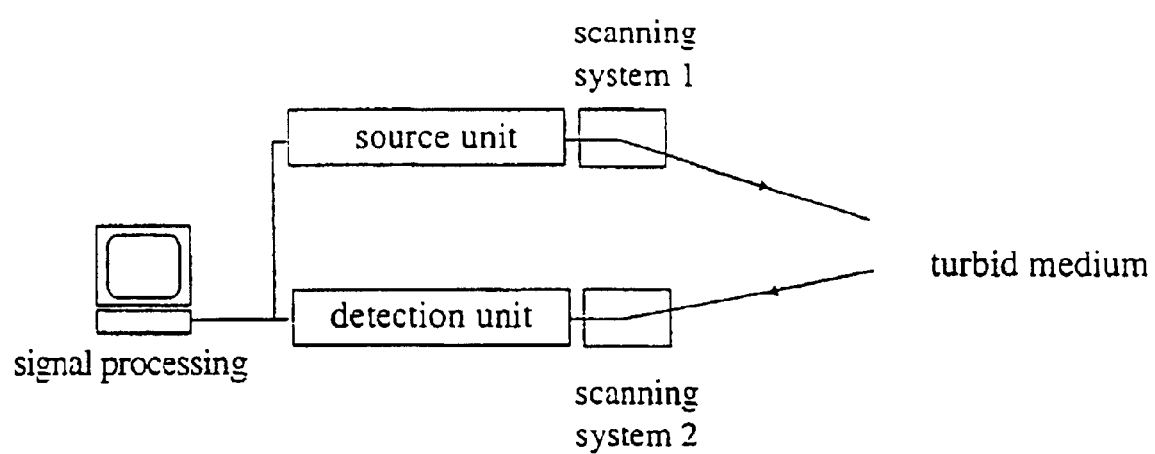

The third embodiment is described in FIG. 5d and FIG. 5e. The only difference with the first and second embodiment is that non-contact measurements are performed. A collimating system allows for a point-like illumination on the turbid medium. An imaging system enables the measurement of the spatial distribution of the reflectance. The detectors can be either an array (1D or 2D) of detectors (FIG. 5d) with optional scanning 1 and 2 which can operate separately or can be confounded in a single scanner, or a single detector (FIG. 5e). In this last case, an scanning device is used to obtain the spatially-resolved reflectance. A fiber bundle, multicore fiber or relay optics (grin rod or multiple lenses) can be put between the focal point of the imaging system and the detector(s). The different type of sources and detectors cited in example for the first embodiment can be used for the third embodiment.

Spatial images of the parameters $\mu_a$, $\mu_s'$ and γ can be obtained by a series of measurements at different locations, that we call multi-site measurements. Some mechanical or optical scanning device can be used for this purpose. The resolution of such images is on the order of the mean source-detector separation used for a single site measurement. All three embodiments can be expanded to perform multi-site measurements, by duplicating and/or multiplexing the illuminating or measuring devices. For example, the optical fiber probes shown in FIG. 6, can be duplicated and put side by side. The scanning system described in the third embodiment can also be expanded to perform multi-site measurements.

4. Normalization and Calibration

The differences of transmission between each fiber are corrected by performing a measurement on a turbid phantom illuminated uniformly.

The background light, measured with the light source turned off, must be subtracted from the signal.

In order to perform absolute intensity measurements, a calibration is performed on a turbid medium of known optical properties. Examples of such a medium are: 1) solid or liquid turbid medium which properties have been measured by other techniques, or reported in the literature, 2) water suspension of microsphere of known size distribution and refractive index. Absorbing dye may be added to the suspension. In case 2) the scattering properties are calculated from Mie theory, and the absorption coefficient is assumed to be equal to the water absorption coefficient, if no absorbing dye is added. If an absorbing dye is used, the absorption coefficient can be measured by a spectrophotometer, before mixing the solution with any scattering materials.

A Monte Carlo simulation is performed with the optical properties of the calibration sample. The simulation is then divided by the experimental reflectance performed on the calibration sample. The result, that must be independent of the source-detector separation, is defined as the calibration factor. Each new measurement is multiplied by the calibration factor.

An example of a measurement, after calibration, is shown in FIG. 7. The measurement was performed with the apparatus described in the first embodiment, with a probe similar to the one described in FIG. 6a. A prior calibration was performed on a solid turbid medium, which optical properties were measured by another technique (frequency domain measurement, cf. Welch, A. J.; van Gemert, M. J. C., Optical Thermal Response of Laser Irradiated Tissue; Plenum Publishing Corp., New York, 1995, and references therein). The sample was a water suspension of polystyrene microsphere of 1 μm diameter. The measurement is compared to a Monte Carlo simulation performed with the scattering properties calculated from Mie theory and absorption coefficient of water. FIG. 7 shows an excellent agreement between the measurement and the simulation, which confirm the validity of our simulation model, experimental measurement and calibration.

5. Signal Processing 5.1. Control of the Homogeneity of the Area Probed

Artifacts during a measurement, for example due to bad contact between the probe and the sample, or heterogeneity of the sample, can be detected by the following optional procedure. Two illuminating fibers are disposed symmetrically in regard to the collecting fibers (see FIG. 6b). If the sample is homogeneous, the reflectance curve should be identical with either illuminating fiber. Therefore, heterogeneity of the investigated region or obstructions beneath the fibers are detected by comparing the two curves. If the two curves are sufficiently close, the measurement is validated and the average of the two curves is calculated.

5.2. Smoothing Procedure and Computation of the Derivative of the Curve

Functions in the form $m_1 \rho^{m_2} \exp(m_3 \rho)$ were always found to fit well Monte Carlo simulations for a restricted range of distances. Therefore, a smoothing of the experimental reflectance $R(\rho)$ can be processed by fitting $R(\rho)$ to $m_1 \rho^{m_2} \exp(m_3 \rho)$. The determination of the slope of the logarithm $$\frac{\partial}{\partial \rho}(\ln R(\rho, \mu_s, \alpha', \gamma))$$

is also derived from this fit, using the following formula:

$$\frac{\partial}{\partial \rho}(\ln R(\rho, \mu_s, \alpha', \gamma)) = \frac{m_2}{\rho} + m_3 \quad (1.10)$$

The slope of the square root of $R(\rho)$ can also be derived (the use of these slopes are described below in section 5.3):

$$\frac{\partial}{\partial \rho}\sqrt{R(\rho, \mu_s, \mu_1, \gamma)} = \left(\frac{m_2}{\rho} + m_3\right)\left(\sqrt{m_1}\, \rho^{\frac{m_2}{2}} \exp\left(\frac{m_3 \rho}{2}\right)\right) \quad (1.11)$$

5.3. Inverse Problem

The so-called "direct problem" consists in computing the spatially resolved reflectance $R(\rho)$ from the values of the optical coefficients n, $\mu_a$, $\mu_s'$, $\gamma$ involved in a model of propagation of the light in turbid medium and whereby the said "model" incorporates a Legendre polynomial development to the second order of the said "phase function", and whereby the said "phase parameter" $\gamma$ is introduced in the computation as an independent parameter. The so-called "inverse problem" consists in extracting the optical coefficients n, $\mu_a$, $\mu_s'$, $\gamma$ from the spatially resolved reflectance data $R(\rho)$.

We developed different methods to solve the inverse problem, which consists in extracting optical coefficients from the reflectance data.

Method 1.

Monte Carlo simulations show that the measurements of the reflectance intensity $R(\rho)$ and the slope of $\ln R(\rho)$ (denoted $\partial \rho \ln R$), determined at a fixed distance $\rho$, can be used to derive $\mu_s'$ and $\mu_a$ for a given $\gamma$ value. FIG. 8. shows graphically the relationship between $\mu_s'$ and $\mu_a$ and the two parameters $R(\rho=1$ mm$)$ and $|\partial \rho \ln R(\rho=1$ mm$)|$ in the case of $\rho=1$ mm, $\gamma=1.5$ and 1.9. Note that any other choice of $\rho$ is possible, as long as $\rho$ is on the order of 1 mfp'. We see in FIG. 8. that $\mu_s'$ and $\mu_a$ can not be determined uniquely if $\gamma$ is unknown. Further insight for optimizing the inversion strategy is provided by three additional features of FIG. 8.

First, the determination of $\mu_s'$ is only weakly influenced by $\gamma$. Indeed in FIG. 8. the errors induced by error in $\gamma$ are typically 10% for $\mu_s'$ around 1 mm$^{-1}$. Second, although absolute determination of $\mu_a$ is not possible when $\gamma$ is not precisely known, relative absorption changes can be still evaluated. Third, the indetermination of the parameter $\gamma$ may be resolved by the values of $R(\rho)$ and/or $|\partial \rho \ln R(\rho)|$ at other distances. Therefore the following procedure can be used:

(1) determination of $\mu_s'$ and $\mu_a$ from $R(\rho=1$ mm$)$ and $|\partial \rho \ln R(\rho=1$ mm$)|$ for a set of values $\gamma$. For example: $\gamma=1.0, 1.1, 1.2, \ldots, 2.5$.

(2) simulations with the different sets of $\mu_s'$ and $\mu_a$ obtained from point 1).

(3) comparison between the simulations and the reflectance profile for distances $0.3 < \rho < 2$ mm.

This last step allows us to determine the correct values of $\gamma$, $\mu_s'$ and $\mu_a$. Points 1 to 3 can be done iteratively to evaluate $\gamma$ more precisely, using a finer discrimination of $\gamma$ values.

This method described by the iteration of points 1) to 3) corresponds to finding a simulation that fit closely a measured curve $R(\rho)$. This can also be achieved by directly comparing the measured curve $R(\rho)$, with a set of simulations, and finding the simulation that minimize the square of the differences between the measured and simulated curves.

Note also that the use of the reflectance intensity $R(\rho)$ and the slope of $\ln R(\rho)$ is equivalent to the use of two intensities $R(\rho_1)$ and $R(\rho_2)$, measured at two close distances $\rho_1$ and $\rho_2$, respectively.

Method 2.

The inverse problem can also be performed, considering properties of $R(\rho)$ expressed by Equ. (1.8).

Indeed, it can be derived from Equ. (1.9) that the quantity does not depend on the absorption coefficient $\mu_a$:

$$\frac{\partial}{\partial \rho}\sqrt{R(\rho, \mu_1, \mu_c, \gamma)} = \frac{\partial A}{\partial \rho}(\rho, \mu_1, \gamma) \quad (1.12)$$

This property is confirmed in FIG. 9, where the quantity $$\frac{\partial}{\partial \rho}\sqrt{R(\rho, \mu_s, \mu_c, \gamma)},$$

evaluated at $\rho=1$ mm, is plotted as a function of $\mu_s'$ for $\gamma=1$, 1.9 and 2.5 and reduced albedo a'=1, 0.95 and 0.9 (note that any other choice of $\rho$ is possible, as long as $\rho$ is of the order of 1 mfp').

In FIG. 9., the parameter $$\frac{\partial}{\partial \rho}\sqrt{R(\rho, \mu_s, \mu_c, \gamma)}$$

clearly depends on $\mu_s'$ and $\gamma$. In contrast, the dependence on a' is almost negligible.

Therefore, $\gamma$ and $\mu_s'$ can be derived from the parameter $$\frac{\partial}{\partial \rho}\sqrt{R(\rho_1, \mu_s, \mu_c, \gamma)},$$

calculated from the experimental reflectance R($\rho$) (see section 5.2). Simultaneous determination of $\gamma$ and $\mu_s'$ require values of $$\frac{\partial}{\partial \rho}\sqrt{R(\rho, \mu_s, \mu_c, \gamma)}$$

at different distances $\rho$ (at least two). If one of the parameters $\gamma$ or $\mu_s'$ is already known, the determination of the other one can be obtained from the value of $$\frac{\partial}{\partial \rho}\sqrt{R(\rho, \mu_s, \mu_c, \gamma)}$$

at a single distance.

Convenient analytical approximation of $$\frac{\partial}{\partial \rho}\sqrt{R(\rho, \mu_s, \mu_c, \gamma)}$$

can be obtained by fitting Monte Carlo results to polynomial functions. For example, in the case of fixed $\gamma=1.9$, we obtained:

$$\mu_s' = 0.9162 - 52.89x + 1795x^2 - 18155x^3 + 65428x^4 \quad (1.13)$$

where $$x = \frac{1}{2}\frac{\partial}{\partial \rho}\sqrt{R(\rho, \mu_s, \mu_c, \gamma)}$$

at $\rho=1$ mm, x is expressed in [mm$^{-2}$] and $\mu_s'$ is expressed in [mm$^{-1}$].

This results is valid for a probe of refractive index of 1.5 and a sample of refractive index of 1.4, optical fibers of diameter 200 $\mu$m, NA=0.37 (source and collection).

Once $\mu_s'$ and $\gamma$ are calculated from the procedure explained above, $\mu_a$ is calculated from the absolute value of R($\rho$), which highly depends on $\mu_a$. For given $\mu_s'$, $\gamma$ and $\rho$ values, the dependence of reflectance on $\mu_a$ is obtained by Monte Carlo results. From Equ. (1.8) we have:

$$\mu_a = h[\sqrt{\sqrt{R(\rho,\mu'_s,\mu_a,\gamma)}} - f(\gamma, \mu_s')] \quad (1.14)$$

where and are functions given by Monte Carlo simulation. Particularly, they can be well approximated by polynomial functions. For example, for $\gamma=1.9$, probe refractive index of 1.5, sample refractive index of 1.4, optical fibers of diameter 200 $\mu$m, NA=0.37 (source and collection):

$$h = -0.002257 - 8.171y + 268.8y^2 \quad (1.15)$$

$$f = 0.01311 + 0.05184\,\mu_s' - 0.01974\,\mu_s'^2 + 0.003217\,\mu_s'^3 - 0.0001992\,\mu_s'^4 \quad (1.16)$$

where $y = [\sqrt{R(\rho,\mu'_s,\mu_a,\gamma)} - f]$ [mm$^{-1}$], $\mu_a$ is expressed in [mm$^{-1}$].

Method 3

Equ. (1.8) also shows that relative measurements of $\mu_a$, i.e. variation of $\mu_s$ from a known value $\mu_{a0}$, is possible by measuring the variation of the parameter $\sqrt{R(\rho,\mu'_s,\mu_a,\gamma)}$:

$$\sqrt{R(\rho,\mu'_s,\mu_{a0},\gamma)} - \sqrt{R(\rho,\mu'_s,\mu_a,\gamma)} = B(\mu_{a0},\mu'_s) - B(\mu_a,\mu'_s) \quad (1.17)$$

This relation is illustrated in FIG. 10. in the case of $\mu_{a0}=0$, $\rho=1$ mm, $\gamma=1.0$, 1.9 and 2.5, and for a'=1 to 0.83, confirms that the influence of $\gamma$ is weak in the quantity $\sqrt{R\rho,\mu'_s,\mu_{a0},\gamma)} - \sqrt{R(\rho,\mu'_s,\mu_a,\gamma)}$. For known $\mu_s'$, the function B(a') allows for the determination of a relative absorption change $\Delta\mu_a=\mu_a-\mu_{a0}$. FIG. 10. illustrates the case $\mu_{a0}=0$, but any other value of $\mu_{a0}$ is possible. The interesting point is that B(a') does not depend on the phase function.

What is claimed is:

1. A method for local and superficial characterization of a turbid medium using the following parameters:
    1) the refractive index n of the turbid medium
    2) the absorption coefficient $\mu_a$ of the turbid medium
    3) the reduced scattering coefficient $\mu_s'$ of the turbid medium
    4) the phase function parameter $\gamma=(1-g_2)/(1-g_1)$ of the turbid media, where $g_1$ and $g_2$ are the first two moments of the Legendre polynomial development of the phase function p, the method comprising the steps of:
        measuring the spatially-resolved reflectance R($\rho$) of the turbid medium ($\rho$ being the source-detector distance) using an illumination beam as a source and an optical detector,
        mathematically processing R($\rho$) to compute at least one of the said parameters: n, $\mu_a$, $\mu_s'$, $\gamma$ and/or the variations, in time and/or space, of at least one of the said parameters: $\Delta$n, $\Delta\mu_a$, $\Delta\mu_s'$, $\Delta\gamma$, whereby an "inverse problem", which comprises extracting the optical coefficients from the spatially resolved reflectance data is solved, and whereby a "direct problem" comprises computing the spatially resolved reflectance from the values of the optical coefficients n, $\mu_a$, $\mu_s'$, $\gamma$ involved in a model of propagation of the light in turbid medium and whereby the said "model" incorporates a Legendre polynomial development to the second order of the said "phase function", and whereby the said "phase parameter" $\gamma$ is introduced in the computation as an independent parameter.

2. The method of claim 1, wherein said spatially resolved reflectance is measured by a probe comprising at least one optical fiber carrying the light from the source unit to the turbid medium and at least one optical fiber collecting the reflected light and carrying it to the optical detector, whereby the combination of a variety of emitting fibers and of receiving fibers yields a set of distances $\rho$ at which the reflectance R($\rho$) is measured.

3. The method according to claim 2, wherein the probe is put into contact with the turbid medium.

4. The method according to claim 1, wherein said spatially resolved reflectance R($\rho$) is measured for a set of values of $\rho$, by using a probe composed of optical fibers in any of the following configurations:
    one emitting optical fiber and a set of optical receiving fibers
    a set of optical emitting fibers and one optical receiving fiber
    a set of optical emitting fibers and a set of optical receiving fibers giving the spatially resolved reflectance R(ρ) at a variety of source-detector distances ρ and wherein the emitting and receiving fibers are arranged in one of the following configurations:
- on a line,
- on crossed lines,
- on a circle,
- on an ellipse,
- on crossed ellipses,
- on a disk, a rectangle, or any surface, as a dense and contiguous arrangement of fibers,
- on any pattern resulting from the combination of the above mentioned patterns.

5. The method according to claim 4, wherein said spatially resolved reflectance is measured by an optical and electronic micro-system comprising a collimated or focused beam as illuminating source and 1D or 2D arrays of optical detectors.

6. The method according to claim 5, wherein the optical and electrical micro-system is put into contact with the turbid medium.

7. The method of claim 1, wherein said spatially resolved reflectance is measured by a non-contact system, comprising at least one of the following combination of optical systems:
- a fixed optical system to irradiate the turbid medium with a collimated or focused beam forming the illuminating source and a fixed optical system comprising an imaging system forming the image of the measured area of the turbid medium on a said "optical detector", which can be formed of 1D or 2D array of optical detectors, whereby the array of optical detectors can be one of the following systems:
  - a set of optical fibers,
  - an optical and electronic micro-system (MOEM),
- a fixed optical system for the collimated beam illuminating source and a scanned optical system for the said "optical detector",
- a scanning optical system for the collimated beam illuminating source and a fixed optical system for the said "optical detector",
- a scanning optical system for the collimated or focused beam used as an illuminating source and a scanning optical system for the said "optical detector".

8. The method according to claim 1, wherein the absorption coefficient $\mu_a$ the reduced scattering coefficient $\mu_s'$ and the phase function parameter γ are determined by fitting the measured spatially-resolved reflectance R(ρ, $\mu_s'$, $\mu_a$, γ) to a set of discretized data obtained by using Monte Carlo simulations, or to interpolating functions giving a continuous approximation of the discretized data obtained by Monte Carlo simulations, and whereby said "Monte Carlo simulations" are based on a photon propagation model comprising a phase function approximated by a Legendre polynomial development limited to the second order.

9. The method according to claim 8, wherein one or more of the following signal processing steps are performed:

fitting the measured reflectance R(ρ) by the function:

$$m_1 \rho^{m_2} \exp(m_3 \rho)$$

to give the values of the parameters $m_1$, $m_2$ and $m_3$, assuming that the expression $$R(\rho) = m_1 \rho^{m_2} \exp(m_3 \rho)$$

gives a smoothed expression of the spatially resolved reflectance R(ρ), computing the slopes $$\frac{\partial}{\partial \rho} \sqrt{R(\rho)} \text{ and } \frac{\partial}{\partial \rho}(\ln R(\rho)),$$

or any mathematical combinations of these two latter quantities and R(ρ), from analytical functions using the parameters $m_1$, $m_2$ $m_3$, or by numerical procedures from the expression $$R(\rho) = m_1 \rho^{m_2} \exp(m_3 \rho),$$

computing the values of at least one of the said parameters: n, $\mu_a$, $\mu_s'$, γ and/or the variations, in time and/or space, of at least one of the said parameters: Δn, $\Delta\mu_a$, $\mu_s'$, Δγ from the relationship between the reflectance intensity R(ρ) and the slope of lnR(ρ) (denoted ∂ ρlnR), determined at a fixed distance ρ comparable to the transport mean free path, whereby the computation is made from the data obtained by Monte Carlo simulations, provided that said "Monte Carlo simulations" are based on a photon propagation model comprising a phase function approximated by a Legendre polynomial development limited to the second order.

10. The method according to claim 8, wherein the following signal processing steps are performed:

computing the reduced scattering coefficient $\mu_s'$ and the phase function parameter γ by using the following form of the reflectance:

$$R(\rho) = (A(\rho, \gamma, \mu_s') + B(\mu_a, \mu_s'))^2$$

where the function A(ρ, γ, $\mu_s'$) and B($\mu_a$, $\mu_s'$) depend also on the source and detector characteristics, and the refractive index of the sample, and comprising the steps of:

computing the slopes of the square root of the spatially resolved reflectance $$\frac{\partial}{\partial \rho} \sqrt{R(\rho, \mu_s, \mu_n, \gamma)} = \frac{\partial A}{\partial \rho}(\rho, \mu_s', \gamma),$$

which depends weakly on the absorption coefficient $\mu_a$ for $0.3 < \rho\mu_s' < 5$, for at least two distances ρ, determining the parameters $\mu_s'$ and γ by a polynomial interpolation of the data obtained by Monte Carlo simulations, whereby said "Monte Carlo simulations" are based on a photon propagation model comprising a phase function approximated by a Legendre polynomial development limited to the second order.

11. The method of claim 10, wherein the absorption coefficient $\mu_a$ is determined by using the equation:

$$\mu_a = h[\sqrt{R(\rho, \mu_s', \mu_a, \gamma)} - f(\gamma, \mu_s')]$$

where $f$ and h are continuous functions of the parameters ρ, $\mu_s'$ and γ that can be approximated by a polynomial interpolation of the data obtained by Monte Carlo simulations, whereby said "Monte Carlo simulations" are based on a photon propagation model comprising a phase function approximated by a Legendre polynomial development limited to the second order.

12. The method according to claim 1, wherein the difference $\Delta\mu_a = \mu_a - \mu_{a0}$ between the absorption coefficient $\mu_a$ and a known value $\mu_{a0}$ is computed from the quantity $\sqrt{R(\rho, \mu'_s, \mu_{a0}, \gamma)} - \sqrt{R(\rho, \mu'_s, \mu_a, \gamma)} = B(a') - B(a_0')$, whereby the function $B(a')$ of the albedo a' can be can be approximated by a polynomial interpolation of the data obtained by Monte Carlo simulations, whereby said "Monte Carlo simulations" are based on a photon propagation model comprising a phase function approximated by a Legendre polynomial development limited to the second order, and whereby the calculation can be done for a single $\gamma$ value, because the influence of the phase function parameter and $\gamma$ in $B(a')$ are particularly weak.

13. The method according to claim 1, wherein the illuminating source is a broadband source or a white light source and the detector unit comprises a spectrograph or any wavelength analysis system to measure the wavelength dependence of at least one of the parameters (n, $\mu_a$, $\mu_s'$, $\gamma$).

14. The method according to claim 1, wherein said turbid medium is a biological medium.

15. The method according to claim 1, wherein the measurement and processing is repeated at different locations of the sample, to build images of any one of the said parameters (n, $\mu_a$, $\mu_s'$, $\gamma$).

16. An apparatus using the method of claim 1 for local and superficial characterization of a turbid medium,
   a) comprising a source, a detection unit, reference means, signal processing means, a probe comprising at least one optical fiber connecting said source unit to the turbid medium and at least one optical fiber connecting the turbid medium to the said detection unit, and reference means
   b) where the distance between the source and the detector is close to one transport mean free path.

17. A system comprising three apparatus described in claim 16, and characterized by the fact that the distance between the collimated or focused optical beam used as illuminating source and the emitting point connected to an optical detector varies from 0.1 to 2 mm. for application to biological media and to turbid media having a transport mean free path similar to biological media.

18. A test, where the control of the homogeneity of the sample over the probed area is performed with the apparatus of 16, which can be carried out according to the following procedure: in the apparatus, disposing two illuminating fibers symmetrically in regard to the collecting fibers; comparing the reflectance curves for each illuminating fiber to detect the heterogeneity of the investigated region or obstructions beneath the fibers; and, if the two curves are sufficiently close, validating the measurement and calculating the average of the two curves.

19. A calibration and normalization procedure, which are carried out with the apparatus of claim 16, whereby the following steps are performed:
   1) in order to perform relative intensity measurements, the differences of transmitted intensity between each fiber for the apparatus of claim 15 are determined by performing a measurement on a turbid phantom illuminated uniformly or a diffusing sphere of perfectly uniform properties;
   2) in order to perform absolute intensity measurements, a calibration performed on a turbid medium of known optical properties, which can be realized according to any one of the following recipes:
      a) solid or liquid turbid medium which properties have been measured by other techniques, or reported in the literature,
      b) water suspension of micro-spheres of known size distribution and refractive index.

20. An apparatus using the method of claim 1 for local and superficial characterization of a turbid medium,
   a) comprising an optical and electronic micro-system comprising at least one illuminating source, at least one detector, signal processing means and reference means,
   b) where the distance between the source and the detector is close to one transport mean free path.

21. An apparatus using the method of claim 1 for local and superficial characterization of a turbid medium,
   a) comprising a collimated or focused beam used as an illuminating source, at least an optical detector for the detection unit, a fixed or scanning optical system for the illuminating source and a fixed or scanning optical system for the said "optical detector", signal processing means and reference means,
   b) where the distance between the source and the detector is close to one transport mean free path.

* * * * *